United States Patent [19]

Lachhein et al.

[11] Patent Number: 4,599,207

[45] Date of Patent: Jul. 8, 1986

[54] PROCESS FOR THE PREPARATION OF PHOSPHORUS-CONTAINING CYANOHYDRIN DERIVATIVES

[75] Inventors: Stephen Lachhein, Mörfelden-Walldorf; Hilmar Mildenberger, Kelkheim, both of Fed. Rep. of Germany

[73] Assignee: Hoechst Aktiengesellschaft, Frankfurt am Main, Fed. Rep. of Germany

[21] Appl. No.: 614,846

[22] Filed: May 29, 1984

[30] Foreign Application Priority Data

Jun. 1, 1983 [DE] Fed. Rep. of Germany ....... 3319850

[51] Int. Cl.[4] .............................................. C07F 9/32
[52] U.S. Cl. .................................................. 558/137
[58] Field of Search ......................... 260/453 RZ, 970

[56] References Cited

U.S. PATENT DOCUMENTS

| | | | |
|---|---|---|---|
| 3,726,847 | 4/1973 | Lewis et al. | 260/453 RZ |
| 4,001,352 | 1/1977 | Kleiner et al. | 260/970 |
| 4,052,484 | 10/1977 | Schliebs et al. | 260/970 |
| 4,057,567 | 11/1977 | Friedman et al. | 260/453 RZ |

FOREIGN PATENT DOCUMENTS 11245  5/1980 European Pat. Off. ............ 260/940

*Primary Examiner*—Anton H. Sutto
*Attorney, Agent, or Firm*—Curtis, Morris & Safford

[57] ABSTRACT

The invention relates to a new process for the preparation of compounds of the formula (I)

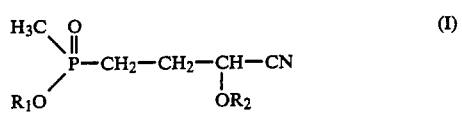

in which $R_1$ denotes alkyl and $R_2$ denotes H, acetyl or propionyl, by addition of compounds of the formula II

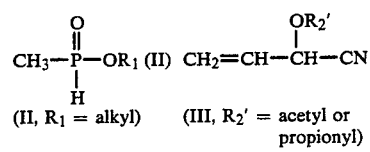

onto compounds of the formula III, using radical-formers, the radical-formers being used being compounds of the general formula IV

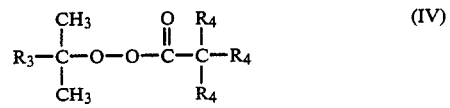

in which $R_3$ denotes alkyl or phenyl and $R_4$ denotes alkyl, the reaction being carried out at temperatures in the range from 50° to 100° C., and, for the preparation of compounds of the formula I where $R_2$ is H, then splitting off the radical $R_2'$. Using this process, the compounds of the formula I are obtained in high yield and particular purity.

7 Claims, No Drawings

PROCESS FOR THE PREPARATION OF PHOSPHORUS-CONTAINING CYANOHYDRIN DERIVATIVES

The present invention relates to a process for the preparation of cyanohydrins of the formula I

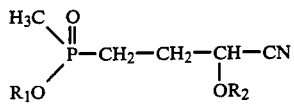

in which
$R_1$ denotes $(C_1-C_6)$alkyl, and
$R_2$ denotes hydrogen, acetyl or propionyl.

Compounds of the formula (I) are used as intermediates for the preparation of phosphinothricin (PTC)

$$CH_3-\underset{\underset{OH}{|}}{\overset{\overset{O}{\|}}{P}}-CH_2-CH_2-\underset{\underset{NH_2}{|}}{CH}-COOH \quad (PTC)$$

which is a herbicide having excellent total herbicidal properties (European patent application No. EP 00 11 245 A1).

Moreover, according to this European patent application, a process for the preparation of the compounds of the formula I is already known, according to which methanephosphonous esters of the formula II undergo addition, with radical catalysis, onto acylated acrolein cyanohydrin compounds of the formula (III).

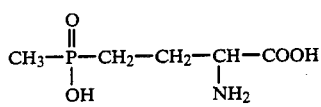

($R_1 = (C_1-C_6)$alkyl)    ($R_2 =$ acetyl or propionyl)

The radical initiators proposed for this are various peroxides, peracid esters, hydroperoxides and azoisobutyronitrile, in particular t-butyl peroctanoate, tbutyl perbenzoate and t-butyl pernonanoate. The process is preferably carried out between 100° and 180° C. The yields are 84–98% of theory based on component (III). The process has the disadvantage that the purities of products are unsatisfactory and that the yields, based on (II), are inadequate. A further disadvantage is that excess methanephosphonous esters (II) contain contaminating products which can only be removed again by elaborate methods.

The yields, based on (II), in the known process are so low because the phosphonous ester (II) undergoes disproportionation reactions which lead to a reduction in yield of recovered phosphonous ester (II), a decrease in the purity of (I) and to a serious loading of the waste gas by the phosphines liberated in the process (K. Sasse in Houben-Weyl: Methoden der org. Chemie (Methods of Org. Chemistry) XII/1, page 64 et seq., Thieme Verlag, Stuttgart 1963).

These disadvantages are eliminated by the present invention. The present invention relates to a process for the preparation of compounds of the abovementioned formula I by addition of compounds of the abovementioned formula II into compounds of the abovementioned formula III in the presence of radical-formers, which process comprises using, as radical-formers, compounds of the general formula IV

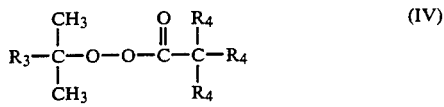

in which $R_3$ denotes $(C_1-C_2)$alkyl or phenyl, and $R_4$ denotes $C_1-C_{10}$alkyl, in particular $(C_1-C_6)$-alkyl, it being possible for the radicals $R_4$ to be identical or different, and carrying out the reaction at temperatures in the range from 65° to 100° C., and, for the preparation of compounds where $R_2$ is H, then splitting off the radical $R_2'$.

For the preparation of compounds of the formula I where $R_2$ is H, it is also possible in principle to use, for $R_2'$ in formula III, other radicals of protective groups, such as the trimethylsilyl radical, or the methoxycarbonyl or ethoxycarbonyl group, which are then split off in the same manner.

The radical initiator substances are distinguished by decomposing at low temperatures into tertiary alkyl radicals which, in the claimed temperature range, have high reactivity and high selectivity in the hydrogen-transfer reactions in the system phosphonous ester (II)-/acrolein cyanohydrin acetate (III) where there is competition.

Radical-formers of this type are not mentioned in European patent application No. 11,245. It was unexpected that exactly the radical-formers of the formula (IV) to be used according to the invention are distinguished by high selectivity. In principle, a possible side reaction is attack by the radical, which has been generated from the radical-former, on the compounds of the formula (III) with the formation of allyl radicals which would inhibit the radical chain reaction (see, for example Vollmert, Grundriss der Makromolekularen Chemie (Outlines of Macromolecular Chemistry) page 58, Springer Verlag, 1962).

Dialkyl peroxides, dialkyl peroxydicarbonates or azoisobutyronitrile, which have low energies of dissociation, so that, for this reason, they should be utilizable in the claimed temperature range, are unsuitable for the present process or they lead to unsatisfactory yields.

Since the radical-formers of the formula (IV) can advantageously be employed at low reaction temperatures between 50° and 100° C., disproportionation reactions of the phosphorus component II are suppressed. By this means, the yields relative to component II, and the purity of the product of the formula (I), are considerably higher than with known processes.

The yields by the process according to the invention are 95 to 99% relative to component III, and 89–95% relative to component II. The purities of the products I are 92 to 95%. The starting compound (II) which has been distilled out of the reaction solution can be used again without purification for a new reaction.

The following compounds are preferably employed as radical-formers of the formula IV: tert.-butyl perpivalate, tert.-amyl perpivalate, tert.-butyl perneodecanoate, tert.-amyl perneodecanoate and cumyl perneodecanoate. The said perneodecanoates (products supplied by Peroxid-Chemie GmbH) are in the form of mixtures of the following formula (IV'):

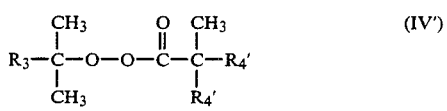

in which $R_3$ has the abovementioned meaning, and the two radicals $R_4'$ each denote $(C_1-C_6)$alkyl with the condition that the number of carbon atoms in the two radicals together totals 7.

The reaction is preferably carried out in the temperature range between 65° and 95° C., and is particularly preferably carried out between 70° and 85° C. The process is advantageously carried out in an inert atmosphere, for example using nitrogen or argon as protective gas. Furthermore, it is possible, even though unnecessary, to work under reduced pressure.

In a particular embodiment of the invention, the process is advantageously carried out such that a portion of the radical-former of the formula (IV) or, in place of that, a corresponding part-equivalent of one of the radical initiators mentioned in European patent application No. 11,245 is, before the reaction, mixed with component II, and then component III, together with the remaining amount of the radical-former IV, is added.

The radical $R_2'$ is split off to prepare the compounds of the formula I, where $R_2$ is H, in acid medium, by known methods (McOmie, "Protective Groups in Organic Chemistry", Plenum Press, London 1973).

The examples which follow serve to illustrate the invention.

EXAMPLE 1

Preparation of N-pentyl (3-acetoxy-3-cyanopropyl)methylphosphinate 242.0 g of n-pentyl methanephosphonite are heated to 80° C. under nitrogen, and 0.5 g of tert.-butyl perpivalate is added. 63.9 g of acrolein cyanohydrin acetate mixed with 2.5 g of tert.-butyl perpivalate are added dropwise to this solution within 2.25 hours. After reaction is complete, the mixture is stirred for 5 minutes, and 161.5 g of n-pentyl methanephosphonite are distilled out. (Purity: 91.2%, recovery: 93.4%). 142.1 g of n-pentyl (3-acetoxy-3-cyanopropyl)methylphosphinate (purity 94%; yield 97%) remain.

EXAMPLE 2

Preparation of isobutyl (3-acetoxy-3-cyanopropyl)methylphosphinate (a) 215.2 g of isobutylmethanephosphonite are heated to 80° C. in a flask flushed with nitrogen. 0.5 g of tert.-butyl perpivalate is added to this solution and, with vigorous stirring at 80° C., 63.9 g of acrolein cyanohydrin acetate, which contains 2.5 g of tert.-butyl perpivalate, are added dropwise within 2 hours. After dropwise addition is complete, the mixture is stirred at 80° C. for 5 min and then the excess isobutyl methanephosphonite is removed under high vacuum. After thin-layer distillation under high vacuum, 134.8 g of isobutyl (3-acetoxy-3-cyanopropyl)methylphosphinate are obtained with a purity of 93.5%, corresponding to a yield of 97%. 142.2 g of isobutyl methanephosphonite are recovered with a purity of 96.3%, corresponding to a yield of 91.6%.

(b) 215.2 g of isobutyl methanephosphonite are heated to 76° C. in a flask flushed with nitrogen, 0.5 g of tert.-butyl perpivalate is added, and 63.9 g of acrolein cyanohydrin acetate, in which 2.6 g of tert.-amyl perpivalate are dissolved, are added dropwise, with vigorous stirring at 76° C., within 2.5 hours. After reaction is complete, the mixture is stirred at 76° C. for 5 mintues. The excess isobutyl methanephosphonite is removed under high vacuum. 134.8 g of isobutyl (3-acetoxy-3-cyanopropyl)-methylphosphinate (purity=93%; yield=96%) are obtained. 142.9 g of isobutyl methanephosphonite are recovered with a yield of 92%.

(c) 215.2 g of isobutyl methanephosphonite are heated to 72° C. under nitrogen, and 0.5 g of tert.-amyl perpivalate is added. 63.9 g of acrolein cyanohydrin acetate, in which 3.6 g of tert.-butyl perneodecanoate are dissolved, are added dropwise to this solution, at 72° C., within 2.5 hours. After addition is complete, the mixture is stirred at 72° C. for 5 min, and 141.2 g of isobutyl methanephosphonite are distilled out under high vacuum (recovery: 91%). 137.9 g of 93.6% pure isobutyl (3-acetoxy-3-cyanopropyl)methylphosphinate remain, corresponding to a yield of 98.9%.

(d) 216.0 g of isobutyl methanephosphonite are heated to 85° C. in a flask flushed with nitrogen. 63.9 g of acrolein cyanohydrin acetate, in which 2.5 g of tert.-butyl perpivalate are dissolved, are added dropwise within 2.75 hours. The mixture is stirred for 5 min, and 140.4 g of isobutyl methanephosphonite are distilled out (recovery: 92.5%).

137.1 g of isobutyl (3-acetoxy-3-cyanopropyl)-methylphosphinate (yield 97%; purity 92%) remain.

(e) 208 g of isobutyl methanephosphonite are heated to 80° C. under nitrogen. 0.5 g of tert.-butyl perpivalate is added to the hot reaction solution, and 63.9 g of acrolein cyanohydrin acetate and 2.5 g of tert.-butyl perpivalate are added dropwise within 2.3 hours. The mixture is stirred at 80° C. for 5 min, and 133.9 g of isobutyl methanephosphonite are distilled out under high vacuum (recovery: 91.3%; purity: 97%). 134.6 g of isobutyl (3-acetoxy-3-cyanopropyl)methylphosphinate (yield: 97.8%, purity 95%) are obtained.

(f) 215.2 g of isobutyl methanephosphonite are heated to 70° C. under nitrogen, and 0.5 g of tert.-butyl perpivalate is added. 63.9 g of acrolein cyanohydrin acetate and 4.5 g of cumyl perneodecanoate are added dropwise within 2.5 hours. After reaction is complete, the mixture is stirred for 5 min, and the excess isobutyl methanephosphonite is distilled out. 141.0 g of isobutyl methanephosphonite are obtained (recovery: 91.8%).

136.1 g of isobutyl (3-acetoxy-3-cyanopropyl)-methylphosphinate (yield 98%; purity 94%) remain.

EXAMPLE 3

Preparation of isopentyl (3-acetoxy-3-cyanopropyl)methylphosphinate (a) 235.0 g of isopentyl methanephosphonite are heated to 72° C. under nitrogen. 0.5 g of tert.-amyl perpivalate is added to the solution, and 63.9 g of acrolein cyanohydrin acetate, in which 3.6 g of tert.-butyl pereodecanoate are dissolved, are added dropwise, with vigorous stirring at 72° C., within 2.75 hours. After reaction is complete, the mixture is stirred at 72° C. for 5 min, and 154.8 g of isopentyl methanephosphonite are distilled out. (Recovery: 94.8%). 143.8 g of 93.6% pure isopentyl (3-acetoxy-3-cyanopropyl)methylphosphinate (yield=97.9%) are obtained.

(b) 235.0 g of isopentyl methanephosphonite are heated to 80° C. under nitrogen, and 0.5 g of tert.-butyl perpivalate is added. 63.9 g of acrolein cyanohydrin acetate and 2.5 g of tert.-butyl perpivalate are added drop-wise, with vigorous stirring at 80° C., within 3 hours. After reaction is complete, 155.2 g of 97.5% pure isopentyl methanephosphonite are distilled out under high vacuum. (Recovery: 95%). 141.8 g of isopentyl (3-acetoxy-3-cyanopropyl)methylphosphinate (yield=96.5%; purity=93.6%) are obtained.

COMPARISON EXAMPLE I

Preparation of isobutyl (3-acetoxy-3-cyanopropyl)methyl-phosphinate using di-n-butyl peroxydicarbonate as the radical initiator 208 g of isobutyl methanephosphonite are heated to 75° C. under nitrogen, and 0.5 g of tert.-butyl perpivalate is added. 63.9 g of acrolein cyanohydrin acetate, in which 2.3 g of di-n-butyl peroxydicarbonate are dissolved, are added dropwise within 2.5 hours. The mixture is stirred for 5 min, and the excess isobutyl methanephosphonite is distilled out. 79.2 g of isobutyl (3-acetoxy-3-cyanopropyl)methylphosphinate remain, corresponding to a yield of 59.5%.

COMPARISON EXAMPLE II

Preparation of isobutyl (3-acetoxy-3-cyanopropyl)methyl-phosphinate according to European patent No. A-11 245

210.5 g of isobutyl methanephosphonite are heated to 115° C. in a flask which is well flushed with nitrogen, and 63.9 g of acrolein cyanohydrin acetate, which contains 2.5 g of tert.-butyl peroctanoate, are added dropwise to this solution at 115° C. within 2.5 hours. After dropwise addition is complete, the mixture is stirred at 115° C. for 5 min and then the excess isobutyl methanephosphonite is distilled out. 134.8 g of isobutyl (3-acetoxy-3-cyanopropyl)methylphosphinate, which is 86.5% pure, are obtained, corresponding to a yield of 89.4% of theory. 118.9 g of isobutyl methanephosphonite are recovered, corresponding to a yield of 79.4% of theory.

We claim:

1. A process for the preparation of a cyanohydrin of the formula I

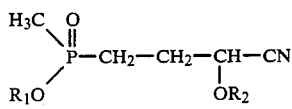

wherein $R_1$ is ($C_1$–$C_6$) alkyl, and $R_2$ is hydrogen, acetyl or propionyl, comprising the addition of a compound of the formula II

wherein $R_1$ is ($C_1$–$C_6$) alkyl with a compound of the formula III

wherein $R_2'$ is acetyl or propionyl, in the presence of a radical forming agent of the formula IV

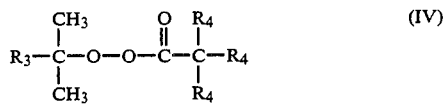

wherein $R_3$ is ($C_1$–$C_2$) alkyl or phenyl, and $R_4$ is ($C_1$–$C_{10}$) alkyl, the $R_4$ radicals being identical or different, at a temperature in the range of 50° to 100° C., and, except in the preparation of a compound of the formula I wherein $R_2$ is H, the radical $R_2'$ is then split off.

2. The process as claimed in claim 1, wherein the radicals $R_4$ in formula IV are ($C_1$–$C_6$) alkyl.

3. The process as claimed in claim 1 wherein the radical forming agent of formula IV is selected from the group consisting of t-butyl perpivalate, tert.-amyl perpivalate, tert.-butyl perneodecanoate, tert.-amyl perneodecanoate, cumyl perneodecanoate and mixtures thereof.

4. The process as claimed in claim 1, wherein the reaction is carried out within the temperature range of from 65° to 95° C.

5. The process as claimed in claim 1 wherein a portion of the radical forming agent of formula IV is initially introduced together with the compound of formula II, and then the compound of formula III together with the remaining amount of the compound of formula IV is added.

6. The process, as claimed in claim 1 wherein the reaction is carried out within the temperature range between 70° and 85° C. in an inert atmosphere under reduced pressure.

7. The process as claimed in claim 1 wherein the radical forming agent is tert.-butylpivalate.

* * * * *